United States Patent [19]

Yanase et al.

[11] Patent Number: 5,679,703
[45] Date of Patent: Oct. 21, 1997

[54] TRICYCLIC COMPOUNDS HAVING ACAT INHIBITING ACTIVITY

[75] Inventors: Masashi Yanase, Numazu; Toshiaki Kumazawa, Shizuoka-ken; Shiro Shirakura, Tokyo; Eiko Oishi, Numazu; Koji Yamada, Sagamihara, all of Japan

[73] Assignee: Kyowa Hakko Kogyo, Co., Ltd., Tokyo, Japan

[21] Appl. No.: 523,843

[22] Filed: Sep. 7, 1995

Related U.S. Application Data

[63] Continuation of Ser. No. 214,535, Mar. 18, 1994, abandoned, which is a continuation-in-part of Ser. No. 121,648, Sep. 16, 1993, abandoned.

Foreign Application Priority Data

Sep. 16, 1992 [JP] Japan ................. 4-246845

[51] Int. Cl.$^6$ ............ A61K 31/335; A61K 31/38; C07D 313/12; C07D 337/12
[52] U.S. Cl. ............ 514/431; 514/450; 549/12; 549/354
[58] Field of Search ............ 549/12, 354; 514/431, 514/450

[56] References Cited

U.S. PATENT DOCUMENTS

| | | | |
|---|---|---|---|
| 4,868,210 | 9/1989 | Trivedi et al. | 514/539 |
| 4,882,351 | 11/1989 | Oshima et al. | 549/12 |
| 5,340,807 | 8/1994 | Kumazawa et al. | 549/354 |

Primary Examiner—Bernard Dentz
Attorney, Agent, or Firm—Antonelli, Terry, Stout & Kraus, LLP.

[57] ABSTRACT

Disclosed is a tricyclic compound represented by formula (I):

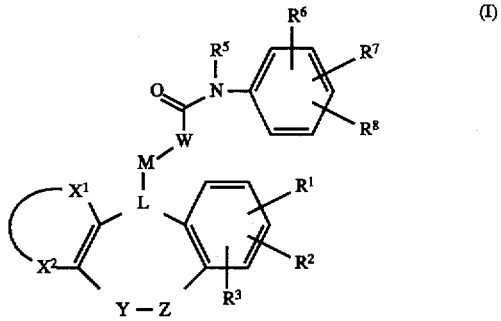

where

- $X^1$-$X^2$ represents CH=CH—CH=CH, CH=CH—CH=N or S—CH=CH;
- Y—Z represents $CH_2$—O or $CH_2$—S; then
- L—M represents C=$CR^9$ (in which $R^9$ represents hydrogen or lower alkyl) or CH—$CR^{10}R^{11}$ (in which each of $R^{10}$ and $R^{11}$ independently represents hydrogen or lower alkyl);
- W represents $NR^4$ (in which $R^4$ represents hydrogen or lower alkyl) or O;
- each of $R^1$, $R^2$ and $R^3$ independently represents hydrogen, lower alkyl, lower alkoxy, halogen, nitro, amino or mono or di-lower alkyl-substituted amino;
- $R^5$ represents hydrogen or lower alkyl;
- each of $R^6$, $R^7$ and $R^8$ independently represents hydrogen, halogen, lower alkyl or lower alkoxy;
- provided that when Y—Z represents CH=CH or $CH_2CH_2$, then L—M represents C=$CR^9$ (in which $R^9$ has the same meaning as defined above), or CH—$CR^{10a}R^{11a}$ (in which each of $R^{10a}$ and $R^{11a}$ represents lower alkyl of $R^{10}$ and $R^{11}$);

and a pharmaceutically acceptable salt thereto.

The compound and its salt have an ACAT inhibiting activity and are expected to have preventive and therapeutic effects on hyperlipemia and arteriosclerosis.

7 Claims, No Drawings

TRICYCLIC COMPOUNDS HAVING ACAT INHIBITING ACTIVITY

CROSS-REFERENCE TO RELATED APPLICATION

This application is a continuation application of application Ser. No. 214,535, filed Mar. 18, 1994 (now abandoned), which application is a continuation-in-part application of application Ser. No. 121,648, filed Sep. 16, 1993 (now abandoned).

BACKGROUND OF THE INVENTION

The present invention relates to tricyclic compounds having acyl coenzyme A:cholesterol acyltransferase (hereinafter referred to as ACAT) inhibiting activity. The compounds are useful for the treatment of hyperlipemia and arteriosclerosis.

Myocardial infarction or cerebral infarction caused by arteriosclerosis has been ranked as high mortality in advanced countries, along with cancer. It has thus been desired to develop a medicine for the treatment of arteriosclerosis. Based on the results of many epidemiological investigations, it has already been pointed out that hypercholesterolemia is one of risk factors of arteriosclerosis. It has been reported that development of arteriosclerosis is prevented by reducing cholesterol level in blood serum, inter alia, cholesterol level with low density lipoprotein (LDL).

Cholesterol is supplied in vivo by biosynthesis and absorption. Compounds which inhibit biosynthesis and absorption might reduce cholesterol level in blood serum. As compounds having an activity of inhibiting absorption, nicotinic acid derivatives and sterols originated from plants are known. However, their activity is not sufficient.

Cholesterol is absorbed on epithelial cells of the intestine in its free form, then esterified by ACAT, included in chylomicron, and transported to liver by blood stream in chylomicron form. ACAT plays an important role in accumulation of cholesterol in liver. ACAT is also involved in transformation of macrophage to foam cell. ACAT is thought to cause progression of arteriosclerosis [J. Lipid Res., 26, 647 (1985); Nippon Rinsho (Clinic in Japan), 47, 554 (1989)]. Compounds which inhibit ACAT might inhibit the absorption of cholesterol and accumulation of cholesterol in liver. Therefore, these effects accelerate excretion of cholesterol and consequently reduce cholesterol level in blood serum. Furthermore, such compounds inhibit the formation of foam cells and are thus expected to be effective for the treatment of hyperlipemia and arteriosclerosis.

The compound represented by formula (A) which possesses an ACAT inhibitory activity is disclosed in U.S. Pat. No. 4,868,210.

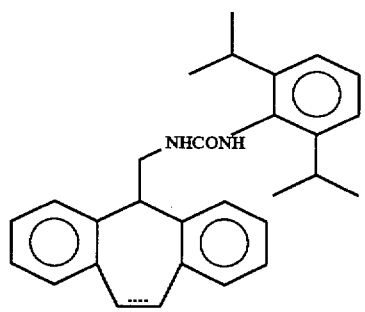

(A)

SUMMARY OF THE INVENTION

An object of the present invention is to provide tricyclic compounds having a strong ACAT-inhibiting activity, which compounds are useful as a medicine for treating hyperlipemia and arteriosclerosis.

The present invention provides tricyclic compounds represented by formula (I):

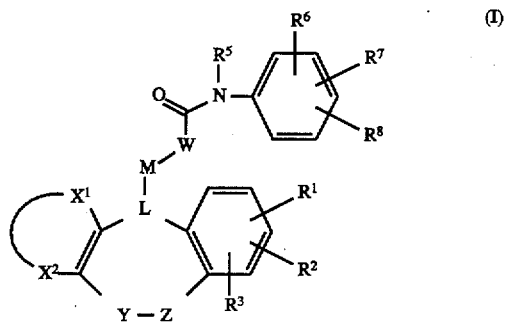

(I)

where $X^1$-$X^2$ represents CH=CH—CH=CH, CH=CH—CH=N or S—CH=CH;

Y—Z represents $CH_2$—O, CH=CH, $CH_2$—$CH_2$ or $CH_2$—S;

L—M represents C=$CR^9$ (in which $R^9$ represents hydrogen or lower alkyl), or CH—$CR^{10}R^{11}$ (in which each of $R^{10}$ and $R^{11}$ independently represents hydrogen or lower alkyl;

W represents $NR^4$ (in which $R^4$ represents hydrogen or lower alkyl) or O;

each of $R^1$, $R^2$ and $R^3$ independently represents hydrogen, lower alkyl, lower alkoxy, halogen, nitro, amino, or mono- or di-lower alkyl-substituted amino;

$R^5$ represents hydrogen or lower alkyl;

each of $R^6$, $R^7$ and $R^8$ independently represents hydrogen, halogen, lower alkyl or lower alkoxy;

provided that when Y—Z represents CH=CH or $CH_2$—$CH_2$, then L—M represents C=$CR^9$ (in which $R^9$ has the same meaning as defined above), or CH—$CR^{10a}R^{11a}$ (in which each of $R^{10a}$ and $R^{11a}$ represents lower alkyl of $R^{10}$ and $R^{11}$);

or a pharmaceutically acceptable salt thereof. The tricyclic compounds represented by formula (I) are hereinafter referred to Compounds (I), and the same shall apply to the numbering of other formulae.

DETAILED DESCRIPTION OF THE INVENTION

In the definitions of the groups in formula (I), the lower alkyl and the alkyl moiety in the lower alkoxy, and mono- or di-lower alkyl-substituted amino means a straight or branched alkyl having 1 to 6 carbon atoms such as methyl, ethyl, propyl, isopropyl, butyl, isobutyl, sec-butyl, tert-butyl, pentyl and hexyl. The halogen includes, for example, fluorine, chlorine, bromine and iodine.

As the pharmaceutically acceptable salt of Compound (I), mention may be made of pharmaceutically acceptable acid addition salts, for example, inorganic acid salts such as hydrochloride, sulfate and phosphate, and organic acid salts such as maleate, fumarate and citrate.

Methods of producing Compound (i) are mentioned below.

Production Method (A):

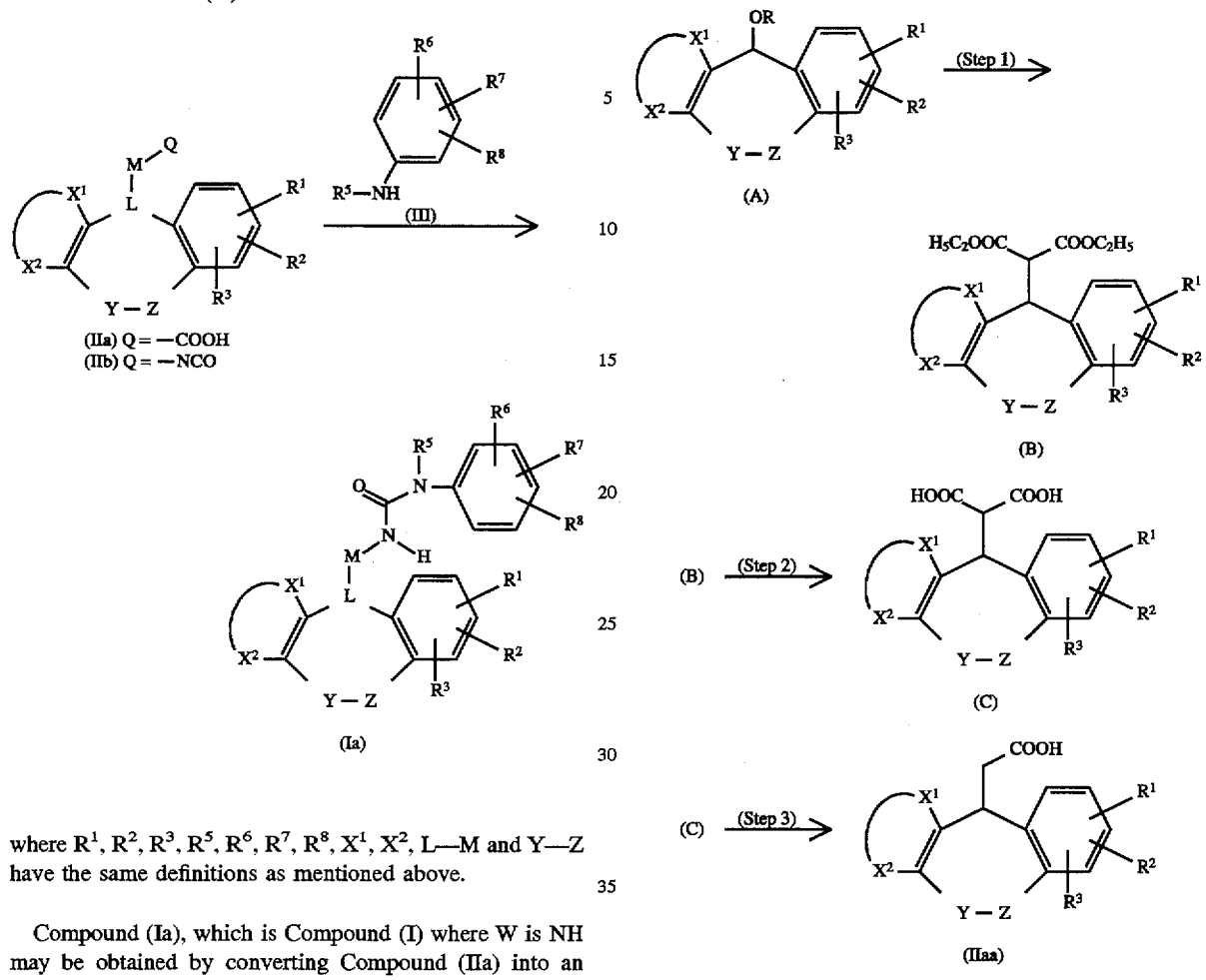

where $R^1$, $R^2$, $R^3$, $R^5$, $R^6$, $R^7$, $R^8$, $X^1$, $X^2$, L—M and Y—Z have the same definitions as mentioned above.

Compound (Ia), which is Compound (I) where W is NH may be obtained by converting Compound (IIa) into an isocyanate derivative (IIb) followed by reacting the derivative (IIb) with Compound (III).

Compound (IIa) is reacted with 1 to 20 equivalents of diphenylphosphoryl azide in the presence of 1 to 20 equivalents of a base such as triethylamine and pyridine in an inert solvent such as dichloromethane, toluene and xylene, at −78° to 60° C. for 0.1 to 24 hours to give Compound (IIb). Compound (IIb) is reacted with 1 to 10 equivalents of Compound (III) in an inert solvent such as dichloromethane, toluene and xylene, optionally in the presence of 1 to 20 equivalents of a base such as triethylamine and pyridine, at a suitable temperature falling within the range of from −78° C. to the boiling point of the solvent used, for 0.1 to 24 hours, to give Compound (Ia).

Of the carboxylic acid (IIa) as the starting material in the above-mentioned reaction, those where L—M is C=CR9 (where $R^9$ has the same definition as mentioned above) may be produced in accordance with known methods (Bull. Soc. Chim. Fr., 4364 (1972)).

Of the carboxylic acid (IIa), Compound (IIaa) which is Compound (IIa) where L—M is CH—$CR^{10b}R^{11b}$ (where $R^{10b}$ and $R^{11b}$ each are hydrogen in the definitions of $R^{10}$ and $R^{11}$) may be produced in accordance with the following process.

where $R^1$, $R^2$, $R^3$, $X^1$, $X^2$ and Y—Z have the same definitions as mentioned above; and R represents lower alkyl, which has the same definition as that of the above-mentioned lower alkyl.

Step 1:
Compound (A) which may be obtained by the method as described in Japanese Published Unexamined Patent Application No. 250/92 or according to a similar method thereto, is reacted with 1 to 20 equivalents of diethyl malonate in dichloromethane in the presence of a catalytic amount to the large excess amount of a Lewis acid such as titanium tetrachloride and optionally in the presence of 1 to 20 equivalents of an amine such as triethylamine, at a suitable temperature falling within the range of from −78° C. to room temperature for 1 to 24 hours, to obtain Compound (B).

Step 2:
Compound (B) is hydrolyzed by an ordinary method, for example, by treating Compound (B) with methanol or ethanol in the presence of an aqueous 10N sodium hydroxide solution at a suitable temperature falling within the range of from 0° C. to the boiling point of the solvent used for 1 to 20 hours, to obtain Compound (C).

Step 3:
Compound (C) is treated with pyridine in the presence of a catalytic amount to a large excess amount of an amine such as piperidine at a suitable temperature falling within the range of from 0° C. to the boiling point of the solvent used for 1 to 20 hours, to obtain Compound (IIaa).

Of carboxylic acid (IIa), Compound (IIab), which is Compound (IIa) where L—M is CH—CR$^{10a}$R$^{11a}$ (in which R$^{10a}$ and R$^{11a}$ each represent lower alkyl of R$^{10}$ and R$^{11}$) may be obtained in accordance with the following process.

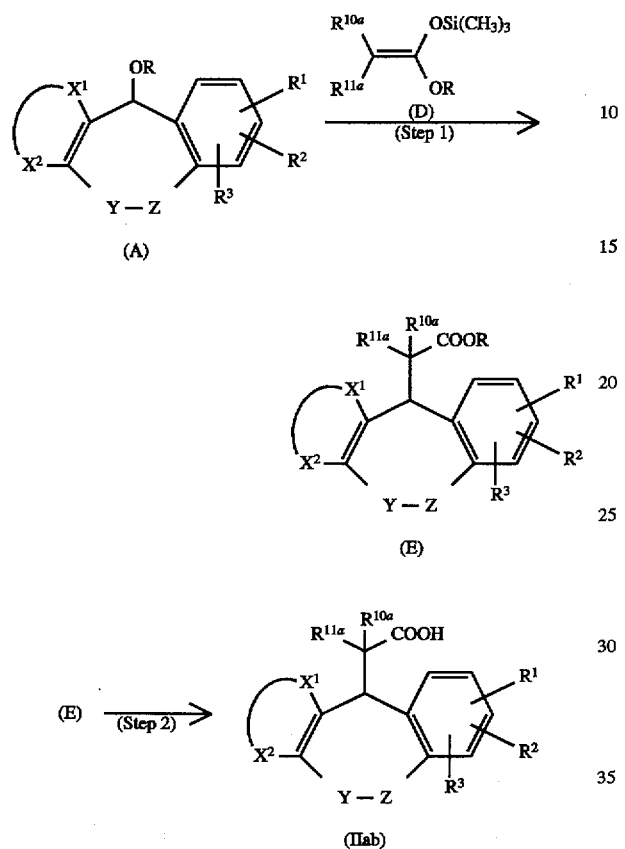

where R, R$^1$, R$^2$, R$^3$, R$^{10a}$, R$^{11a}$, X$^1$, X$^2$ and Y—Z have the same definitions as mentioned above.

Step 1:

Compound (A) which is obtained by the known method as described Japanese Published Unexamined Patent Application No. 250/92 or in accordance with a similar method thereto is reacted with 1 to 20 equivalents of a suitable silylketene-acetal (D) in dichloromethane in the presence of a catalytic amount to a large excess amount, based on Compound (A), of a Lewis acid such as titanium tetrachloride, at a temperature falling within the range of from −78° C. to room temperature for 1 to 24 hours, to obtain Compound (E).

Step 2:

Compound (E) is hydrolyzed by an ordinary method, for example, by treating Compound (E) in dimethylsulfoxide in the presence of 1 to 20 equivalents of potassium t-butoxide at a suitable temperature falling within the range of from 0° C. to the boiling point of the solvent used for 1 to 20 hours, to obtain Compound (IIab).

Production Method (B):

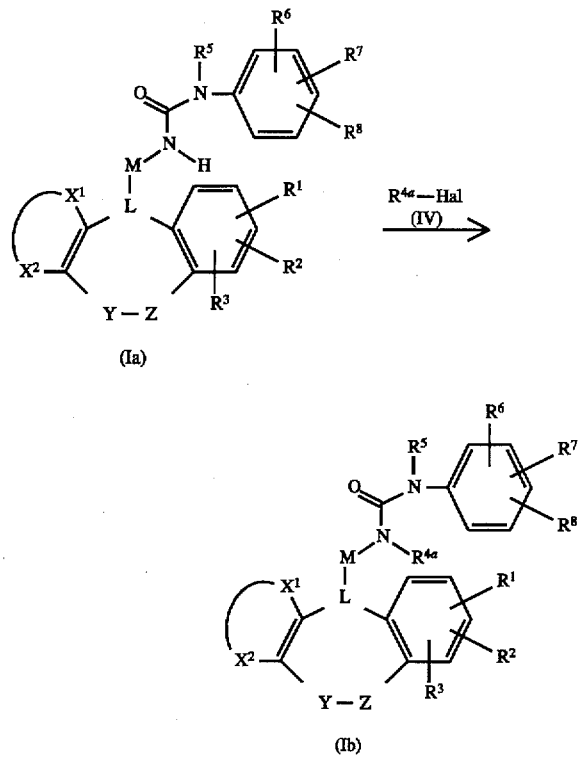

where R$^{4a}$ represents lower alkyl of R$^4$; Hal represents chloriden, bromine or iodine; and R$^1$, R$^2$, R$^3$, R$^5$, R$^6$, R$^7$, R$^8$, X$^1$, X$^2$, L—M and Y—Z have the same definitions as mentioned above.

Of Compound (I), Compound (Ib) which is Compound (I) where W is NR$^{4a}$ (in which R$^{4a}$ has the same definition as mentioned above) may be obtained by reacting Compound (Ia) with 1 to 10 equivalents of Compound (IV) in an inert solvent such as dichloromethane, chloroform, tetrahydrofuran, dimethylformamide, dimethylsulfoxide and toluene optionally in the presence of 1 to 20 equivalents of a base such as potassium t-butoxide, sodium hydride and silver oxide, at a temperature falling within the range of from −78° C. to the boiling point of the solvent used for 0.1 to 24 hours.

Production Method (C):

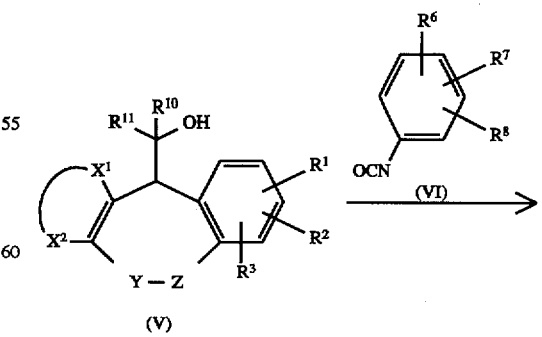

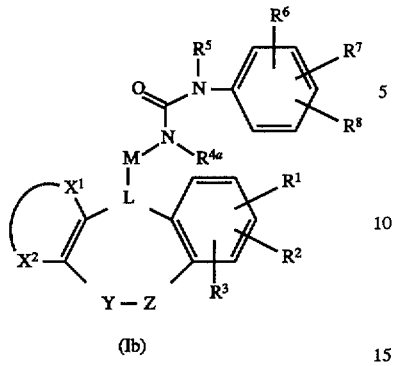

(Ib)

(Va) $R^{10}$ and $R^{11}$=hydrogen
(Vb) $R^{10}$=hydrogen, $R^{11}$=lower alkyl
(Vc) $R^{10}$ and $R^{11}$=lower alkyl where $R^1$, $R^2$, $R^3$, $R^6$, $R^7$, $R^8$, $R^{10}$, $R^{11}$, $X^1$, $X^2$ and Y—Z have the same definitions as mentioned above.

Of Compound (I), Compound (Ic) which is Compound (I) where L—M is CH—$CR^{10}R^{11}$ (in which $R^{10}$ and $R^{11}$ have the same definitions as mentioned above) and W is O may be obtained by reacting Compound (V) with Compound (VI).

Compound (V) is reacted with 1 to 10 equivalents of Compound (VI) in an inert solvent such as dichloromethane, toluene and xylene, optionally in the presence of 1 to 20 equivalents of a base such as triethylamine and pyridine, at a temperature falling within the range of from −78° C. to the boiling point of the solvent used for 0.1 to 24 hours to obtain Compound (Ic).

Of Compound (V) as a starting compound, the alcohol (Va) which is Compound (V) where $R^{10}$ and $R^{11}$ as a starting material are hydrogen may be obtained in accordance with the following process.

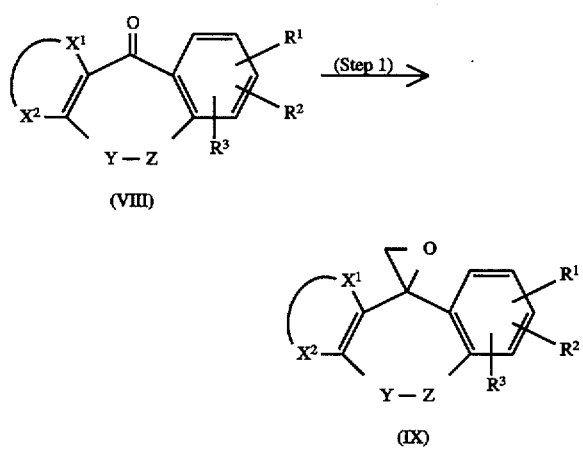

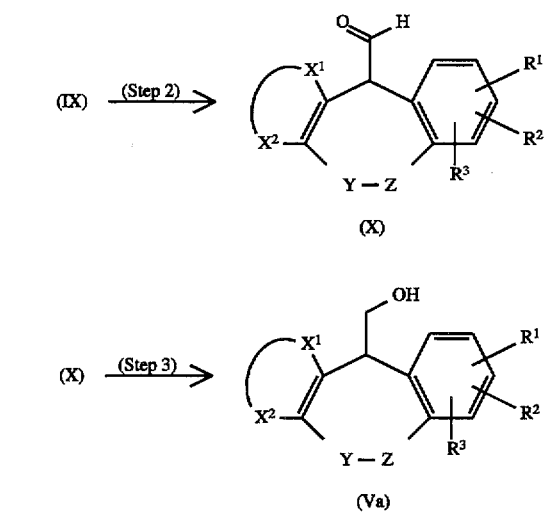

where $R^1$, $R^2$, $R^3$, $X^1$, $X^2$ and Y—Z have the same definitions as mentioned above.

Step 1:

Compound (VIII) to be obtained by a known method as described in German Patent 1,294,970 or in accordance with a similar method thereto is reacted with an ylide to be obtained by reacting trimethylsulfonium iodide with 1 to 2 equivalents of sodium hydride, in a mixed solvent of dimethylsulfoxide-tetrahydrofuran at at suitable temperature falling within the range of from −78° C. to room temperature for 1 to 12 hours to obtain Compound (IX).

Step 2:

Compound (IX) is reacted with a catalytic amount of a Lewis acid such as boron trifluoride-ether complex in dichloromethane at a suitable temperature falling within the range of from −78° C. to 0° C. for 10 minutes to 6 hours and then treated with water to obtain Compound (X).

Step 3:

Compound (X) is reacted with 1 to 10 equivalents of sodium borohydride in a solvent such as methanol or ethanol at a suitable temperature falling within the range of from −30° C. to room temperature for 0.1 to 24 hours to obtain Compound (Va).

Of Compound (V), the alcohol (Vb) which is Compound (V) where $R^{10}$ is hydrogen and $R^{11}$ is lower alkyl, and the alcohol (Vc) which is Compound (V) where $R^{10}$ and $R^{11}$ are lower alkyl can be obtained in accordance with the following process.

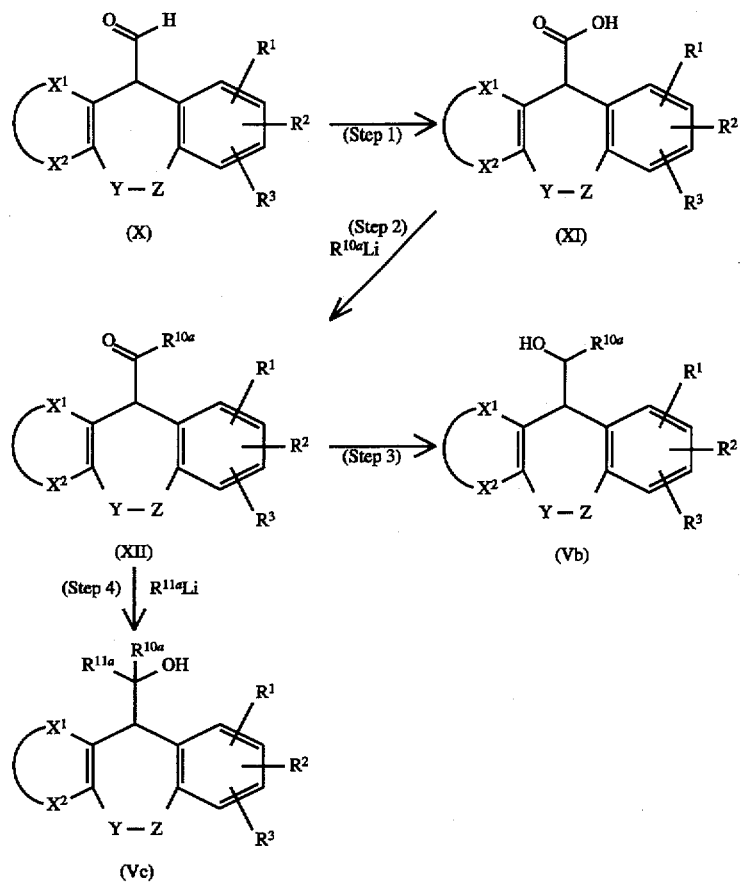

where $R^1$, $R^2$, $R^3$, $R^{10a}$, $R^{11a}$, $X^1$, $X^2$ and Y—Z have the same definitions as mentioned above.

Step 1:

Compound (X) can be converted into Compound (XI) by conventional oxidation using as an oxidizing agent, for example, chromic acid or potassium permanganate. For example, Compound (XI) can be obtained by reacting Compound (X) with an excess of Jones reagent in acetone at an appropriate temperature of from −60° to 0° C.

Step 2:

Compound (XII) can be obtained by reacting Compound (XI) with an excess of an organometallic reagent, for example, alkyl lithium reagent $R^{10a}Li$ in tetrahydrofuran at an appropriate temperature of from −78° to 0° C.

Step 3:

Compound (Vb) can be obtained by reacting Compound (XII) with 1 to 10 equivalents of sodium borohydride in a solvent such as methanol or ethanol at a suitable temperature falling within the range of from −30 to room temperature for 0.1 to 24 hours.

Step 4:

Compound (Vc) can be obtained by reacting Compound (XII) with an excess of an organometallic reagent, for example, alkyl lithium reagent $R^{11a}Li$ (where $R^{11a}$ is lower alkyl which is the same as or different from $R^{10a}$) in the presence of a catalytic amount of cerium trichloride in tetrahydrofuran at an appropriate temperature of −78° to 0° C.

Production Method (D):

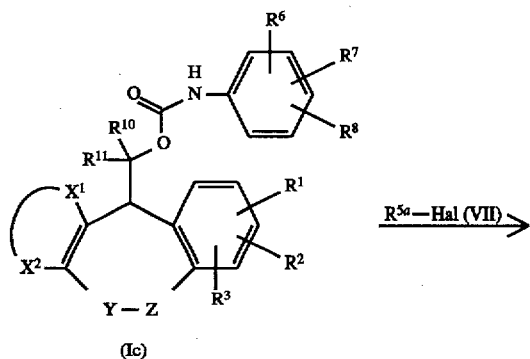

-continued

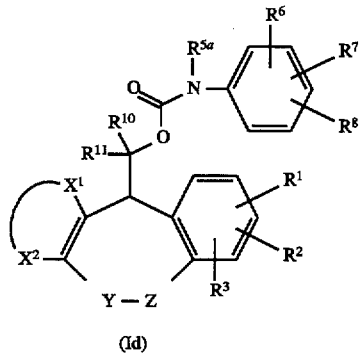

(Id)

where $R^{5a}$ represents lower alkyl of $R^5$; $R^1$, $R^2$, $R^3$, $R^6$, $R^7$, $R^8$, $X^1$, $X^2$, Hal and Y—Z have the same definitions as mentioned above.

Of Compound (I), Compound (Id) which is Compound (I) where $R^5$ is lower alkyl may be obtained by reacting Compound (Ic) with Compound (VII) in accordance with the production method (B).

The intermediates and the desired compounds in the processes described above can be isolated and purified by methods for purification conventionally used in organic synthesis chemistry, for example, filtration, extraction, washing, drying, concentration, recrystallization, various chromatographies, etc. The intermediates can be served for the next reaction without any particular purification.

Where it is desired to obtain the salts of Compound (I), the salts may be purified as they are when the product is obtained in a salt form. Where the product is obtained in a free form, the product is dissolved or suspended in an appropriate solvent and an acid or a base is added to the solution or suspension to form its salt.

Compound (I) has, for example, E/Z geometric isomers. The present invention includes all possible isomers, including such geometric isomers, and their mixtures. If separation of E/Z isomers from each other is desired, the isomers may be, isolated and purified by suitable fractionation methods, for example, by fractionating crystallization, fractionating precipitation or fractionating dissolution.

Compound (I) and its pharmaceutically acceptable salt thereof may be present in the form of adducts with water or various solvents. These adducts are also included in the present invention.

Specific examples of Compound (I) obtained by the respective processes are shown in Table 1.

TABLE 1

(I)

| Compound No. | Y—Z | L—M | W | $R^1$ | $R^2$ | $R^3$ | $R^5$ | $R^6/R^7/R^8$ |
|---|---|---|---|---|---|---|---|---|
| 1 | $CH_2-O$ | $CH-CH_2$ | NH | 2-Me | H | H | H | 2,6-iPr |
| 2 | $CH_2-O$ | $CH-CH_2$ | NH | 2-Br | H | H | H | 2,6-iPr |
| 3 | $CH_2-O$ | $CH-CH_2$ | NH | 1-Me | 2-Br | 3-Me | H | 2,6-iPr |
| 4 | $CH_2-O$ | C=CH | NH | H | H | H | H | 2,6-iPr |
| 5 | $CH_2-CH_2$ | C=CH | NH | H | H | H | H | 2,6-iPr |
| 6 | $CH_2-O$ | $CH-CH_2$ | O | H | H | H | H | 2,6-iPr |
| 7 | $CH_2-O$ | $CH-CH_2$ | NH | H | H | H | H | 2,6-iPr |
| 8 | $CH_2-O$ | $CH-CH_2$ | NH | 2-Br | H | H | H | 2,4-F |
| 9 | $CH_2-O$ | $CH-CH_2$ | NH | 2-Me | H | H | H | 2,4,6-F |
| 10 | $CH_2-O$ | $CH-CH_2$ | NH | 2-Br | H | H | H | 2,4,6-F |
| 11 | $CH_2-O$ | $CH-CH_2$ | NH | 2-Br | H | H | H | 2,4,6-Me |
| 12 | $CH_2-O$ | $CH-CH_2$ | NH | 2-Br | H | H | H | 2,4,6-OMe |
| 13 | $CH_2-O$ | $CH-CH_2$ | NH | 2-OMe | H | H | H | 2,6-iPr |
| 14 | $CH_2-O$ | $CH-CH_2$ | NH | 2-Br | H | H | H | 3,5-tBu, 4-OH |
| 15 | $CH_2-O$ | $CH-CH_2$ | NH | 2-Br | 4-NMe₂ | H | H | 2,6-iPr |
| 16 | $CH_2-O$ | $CH-CMe_2$ | NH | H | H | H | H | 2,4,6-OMe |
| 17 | $CH_2-O$ | $CH-CMe_2$ | NH | 2-Br | H | H | H | 2,4,6-OMe |

In the Table, Me is methyl, iPr is isopropyl and tBu is tert-butyl. The numbering of the compounds therein corresponds to those of Example hereinafter.

The pharmaceutical effects of Compound (I) is explained below.

Text Example 1

Test for Acute Toxicity

Groups of 3 male ddy strain mice weighing 20±1 g were used. The test compounds were orally administered. Seven days after administration, the mortality was observed and the minimum lethal dose (MLD) was determined. The results are given in Table 2.

TABLE 2

| Compound No. | Acute Toxicity (MLD) (mg/kg) |
|---|---|
| 2 | >300 |
| 5 | >300 |

Test Example 2

ACAT Inhibiting Activity Test

The ACAT inhibiting activity test using cells of human cultured cell line HepG2 was carried out in accordance with the method of Goldstein et al as described in Methods Enzymology, 98, 241, 1983. 5×10$^5$ cells/well of human cultured cell line HepG2 were pre-cultured in 5% LPDS (rabbit lipoprotein-deficient serum)-DMEM (Dulbecco Modified Eagle Medium) overnight, and the medium was changed for a fresh 5% LPDS-DMEM (1 ml/well). To the medium having the cells were added 3 µl, as a whole, of cholesterol and 25-OH-cholesterol as dissolved in ethanol (with the final concentration being 10 µg/ml and 5 µg/ml, respectively) and 10 µl of a test compound (shown in Table 3 below) as dissolved in methanol (with the final concentration being $10^{-6}$M). The cells were cultured for 4 hours. Then, 10 µl (0.42 µCi/0.1 µmol/well) of [$^{14}$C]-oleic acid-BSA (bovine serum albumin) complex was added to the medium, and the cells were cultured for further 2 hours. After the cultured cells were washed, the lipid of the cells was extracted with 0.5 ml/well of hexane/isopropanol (3/2) containing [3H]-cholesterol oleic acid 2000 dpm. The extract was dried to a solid under reduced pressure and the solid was fractionated by silica gel thin layer chromatography using a developing solvent of petroleum ether/diethyl ether/acetic acid (170/30/1) whereupon the radioactivity of the spot of the cholesterol ester was measured with a liquid scintillation counter. Subtracting the radioactivity of the blank test to which cholesterol and 25-OH-cholesterol were not added from the radioactivity as measured above gives the radioactivity of the test compound. The ACAT inhibiting activity of the test compound was calculated from the following equation, based on the radioactivity of the control group as obtained in the same manner as above without using the test compound.

TABLE 3

ACAT Inhibition (%) =
{[(Radioactivity of Control Group) − (Radioactivity of Test Compound)]/(Radioactivity of Control Group)} × 100
The results obtained are shown in Table 3 below.

| Compound No. | Percentage of ACAT Inhibition (%) ($10^{-6}$M) |
|---|---|
| 1 | 99 |
| 2 | 98 |
| 3 | 97 |
| 4 | 93 |
| 5 | 94 |
| 6 | 40 |

Test Example 3

Inhibition effect on serum cholesterol level in hamster with dietary hyperlipemia Golden hamster (SLC, male, age of 6 weeks) was made free access to feed containing 2% cholesterol for 3 days. Compound 2 was suspended in olive oil and orally administered once a day in a dose of 10 mg/kg during the feeding (A: Test Group administered with Compound 2 B: Control Group administered with olive oil only). In Group C, feed from cholesterol was fed for 3 days. On the fourth date, blood sample was collected from the descending aorta under pentobarbital anesthesia and cholesterol level in serum was determined. The total cholesterol level in serum of each group was determined and the inhibition rate for the test compound was calculated according to the following equation to be 95.9%.

$$\text{Inhibition rate}(\%) = \frac{B-A}{B-C} \times 100$$

Compound (I) or its pharmaceutically acceptable salt may be administered singly as they are, but it is generally preferred that these compounds be administered in the form of various pharmaceutical preparations. These pharmaceutical preparations can be used for animals and human beings.

The most effective administrative route is chosen from oral and parenteral administration such as intrarectal, topical, intranasal, intraocular, intrabuccal, subcutaneous, intramuscular and intravenous routes, etc.

As the form of administration, mention may be made of a capsule, a tablet, a granule, a powder, a syrup, an emulsion, a suppository, an injection, etc.

A liquid preparation suitable for oral administration, for example, an emulsion and a syrup can be prepared using water; sugars such as sucrose, sorbitol, fructose, etc.; glycols such as polyethylene glycol, propylene glycol, etc.; oils such as sesame oil, olive oil, soybean oil, etc.; antiseptics such as p-hydroxybenzoic acid esters, etc.; flavors such as strawberry flavor, pepper mint, etc. Further a capsule, a tablet, a powder and a granule, etc. can be prepared using an excipient such as lactose, glucose, sucrose, mannitol, etc.; a disintegrator such a starch, sodium alginate, etc.; a lubricant such as magnesium stearate, talc, etc.; a binder such as polyvinyl alcohol, hydoxypropyl cellulose, gelatin, etc.; a surfactant such as an aliphatic ester, etc.; a plasticizer such as glycerine, etc.

A preparation suitable for parenteral administration is a sterile aqueous preparation containing Compound (I), and preferable isotonic to blood of recipient. For example, with an injection, a solution for injection is prepared using carriers composed of a saline solution, a glucose solution or a mixture of saline and glucose solution.

A preparation for rectal administration is provided as a suppository using conventional carriers, for example, cacao fat, hydrogenated fat or hydrogenated fat carboxylic acid, etc.

Further these parenteral preparations may also be added with one or more auxiliary components such as a diluent, a flavor, an antiseptic (including an antioxidant), an excipient, a disintegrator, a lubricant, a binder, a surfactant, a plasticizer and the like.

Effective dose and number of administration of Compound (I) or pharmaceutically acceptable salt thereof vary depending upon administration route, age, body weight and conditions of patients. In general, daily dose for oral admin-

EXAMPLE 1

N-(2,6-diisopropylphenyl)-N'-(2-methyl-6,11-dihydrodibenz[b,e]oxepin-11-ylmethyl)urea (Compound 1)

2.0 g of 2-methyl-6,11-dihydrodibenz[b,e]oxepin-11-acetic acid was dissolved in 40 ml of toluene, and 2.52 ml of diphenylphosphoryl azide and 3.12 ml of triethylamine were added thereto at room temperature and stirred for 3.5 hours at the same temperature and then for further one hour at 100° C. The reaction mixture was cooled to room temperature, and 1.92 g of 2,6-diisopropylaniline hydrochloride and 5.0 ml of triethylamine were added thereto and stirred for 30 minutes and then for further 4 hours at 100° C. The reaction mixture was cooled to room temperature, 150 ml of water was added thereto, and the mixture was extracted with ethyl acetate. The thus obtained organic layer was washed first with 1N hydrochloric acid and then with a saturated saline solution in order, and dried and then concentrated to dryness under reduced pressure. The resulting solid residue was purified by silica gel column chromatography (using an eluting solvent of ⅓ (v/v) ethyl acetate/hexane). The crude product was recrystallized from ethyl acetate to obtain 1.16 g of Compound 1.

IR (KBr tablet; cm$^{-1}$): 3416, 3286, 2962, 2866, 1650, 1537, 1461, 1250

NMR (δ, ppm CDCl$_3$): 2.21 (s, 3H), 4.87 and 5.26 (q, 2H, AB type, J=15.1 Hz)

EXAMPLE 2

N-(2,6-diisopropylphenyl)-N'-(2-bromo-6,11-dihydrodibenz[b,e]oxepin-11-ylmethyl)urea (Compound 2)

2.03 g of Compound 2 was obtained in the same manner as in Example 1, except that 2.0 g of 2-bromo-6,11-dihydrodibenz[b,e]oxepin-11-acetic acid and 1.54 g of 2,6-diisopropylaniline hydrochloride were used.

IR (KBr tablet; cm$^{-1}$): 3416, 3278, 2962, 1642, 1533, 1255

NMR (δ, ppm CDCl$_3$): 4.88 and 5.31 (q, 2H, AB type, J=14.9 Hz)

EXAMPLE 3

N-(2,6-diisopropylphenyl)-N'-(2-bromo-1,3-dimethyl-6,11-dihydrodibenz[b,e]oxepin-11-ylmethyl)urea (Compound 3)

1.87 g of Compound 3 was obtained in the same manner as in Example 1, except that 2.0 g of 2-bromo-1,3-dimethyl-6,11-dihydrodibenz[b,e]oxepin-11-acetic acid and 1.82 g of 2,6-diisopropylaniline hydrochloride were used.

IR (KBr tablet; cm$^{-1}$): 3248, 3062, 2960, 1650, 1639, 1544, 1304

NMR (δ, ppm CDCl$_3$): 2.33 (s, 3H), 2.52 (s, 3H), 4.88 and 5.28 (q, 2H, AB type, J=15.6 Hz)

EXAMPLE 4

N-(2,6-diisopropylphenyl)-N'-(6,11-dihydrodibenz[b,e]oxepin-11(6H)-ylidene)urea (Compound 4)

0.40 g of Compound 4 was obtained in the same manner as in Example 1, except that 0.59 g of (6,11-dihydrodibenz[b,e]oxepin-11(6H)-ylidene)acetic acid and 0.60 g of 2,6-diisopropylaniline hydrochloride were used.

IR (KBr tablet; cm$^{-1}$): 3390, 3216, 2966, 1692, 1635, 1507, 1309, 1222

NMR (δ, ppm CDCl$_3$): 5.11 (brs, 2H), 5.93 and 6.00 (each s, 1H as combined)

EXAMPLE 5

N-(2,6-diisopropylphenyl)-N'-(10,11-dihydrodibenz[a,d]cyclohepten-5(10H)-ylidene)urea (Compound 5)

2.30 g of Compound 5 was obtained in the same manner as in Example 1, except that 2.0 g of 10,11-dihydrodibenz[a,d]cyclohepten-5(10H)-ylidene)acetic acid and 2.0 g of 2,6-diisopropylaniline hydrochloride were used.

IR (KBr tablet; cm$^{-1}$): 3386, 3212, 2964, 1688, 1632, 1505, 1478, 1276

NMR (δ, ppm CDCl$_3$): 6.03 (s, 1H)

EXAMPLE 6

(6,11-Dihydrodibenz[b,e]oxepin-11-ylmethyl)-(2,6-diisopropylphenyl)carbamate (Compound 6)

1.1 g of 6,11-dihydrodibenz[b,e]oxepin-11-methanol was dissolved in 30 ml of dichloromethane, and 2.7 ml of triethylamine and 2.3 ml of 2,6-diisopropyl isocyanate were added thereto with cooling on ice. The mixture was stirred for 15 hours at room temperature, and 100 ml of water was added to the reaction mixture, and then extracted with dichloromethane. The thus obtained organic layer was washed first with 1N hydrochloric acid and then with a saturated saline solution, dried and concentrated to dryness under reduced pressure. The solid residue was purified by silica gel column chromatography (using an eluting solvent of ⅑ (v/v) ethyl acetate/toluene). The crude product was recrystallized from ethyl acetate to obtain 0.97 g of Compound 6.

IR (KBr tablet; cm$^{-1}$): 3310, 2962, 1705, 1693, 1510, 1493, 1243

NMR (δ, ppm CDCl$_3$): 4.97 and 5.40 (q, 2H, AB type, J=19.0 Hz)

EXAMPLE 7

N-(2,6-diisopropylphenyl)-N'-(6,11-dihydrodibenz[b,e]oxepin-11-ylmethyl)urea (Compound 7)

2.20 g of Compound 7 was obtained in the same manner as in Example 1, except that 2.0 g of 6,11-dihydrodibenz[b,e]oxepin-11-acetic acid and 1.67 g of 2,6-diisopropylaniline were used.

IR (KBr tablet; cm$^{-1}$): 3418, 2932, 1637, 1543, 1491, 1260

NMR (δ, ppm CDCl$_3$): 4.12 (t, 1H, J=7.6 Hz), 4.90 and 5.30 (q, 2H, AB type, J=15.2 Hz)

EXAMPLE 8

N-(2,4-difluorophenyl)-N'-(2-bromo-6,11-dihydrodibenz[b,e]oxepin-11-ylmethyl)urea (Compound 8)

0.71 g of Compound 8 was obtained in the same manner as in Example 1, except that 1.0 g of 2-bromo-6,11-dihydrodibenz[b,e]oxepin-11-acetic acid and 0.46 g of 2,4-difluoroaniline were used.

IR (KBr tablet; cm$^{-1}$): 3278, 2608, 1642, 1614, 1509, 1432, 1228

NMR (δ, ppm CDCl$_3$): 4.07 (t, 1H, J=7.6 Hz), 4.95 and 5.40 (q, 2H, AB type, J=14.8 Hz)

EXAMPLE 9

N-(2,4,6-trifluorophenyl)-N'-(2-methyl-6,11-dihydrodibenz[b,e]oxepin-11-ylmethyl)urea (Compound 9)

1.08 g of Compound 9 was obtained in the same manner as in Example 1, except that 1.0 g of 2-methyl-6,11-dihydrodibenz[b,e]oxepin-11-acetic acid and 0.66 g of 2,4,6-trifluoroaniline were used.

IR (KBr tablet; cm$^{-1}$): 3372, 1638, 1546, 1525, 1504, 1447, 1254

NMR (δ, ppm CDCl$_3$): 4.20 (t, 1H, J=7.8 Hz), 4.96 and 5.41 (q, 2H, AB type, J=14.8 Hz)

EXAMPLE 10

N-(2,4,6-trifluorophenyl)-N'-(2-bromo-6,11-dihydrodibenz[b,e]oxepin-11-ylemthyl)urea (Compound 10)

0.44 g of Compound 10 was obtained in the same manner as in Example 1, except that 1.0 g of 2-bromo-6,11-dihydrodibenz[b,e]oxepin-11-acetic acid and 0.53 g of 2,4,6-trifluoroaniline were used.

IR (KBr tablet; cm$^{-1}$): 3252, 1614, 1543, 1523, 1484, 1451, 1231

NMR (δ, ppm CDCl$_3$): 4.19 (t, 1H, J=7.8 Hz), 4.96 and 5.44 (q, 2H, AB type, J=14.7 Hz)

EXAMPLE 11

N-(2,4,6-trimethylphenyl)-N'-(2-bromo-6,11-dihydrodibenz[b,e]oxepin-11-ylmethyl)urea (Compound 11)

0.81 g of Compound 11 was obtained in the same manner as in Example 1, except that 1.0 g of 2-bromo-6,11-dihydrodibenz[b,e]oxepin-11-acetic acid and 0.49 g of 2,4,6-trimethylaniline were used.

IR (KBr tablet; cm$^{-1}$): 2918, 1635, 1610, 1562, 1484, 1233

NMR (δ, ppm CDCl$_3$): 4.10 (t, 1H, J=7.8 Hz), 4.90 and 5.34 (q, 2H, AB type, J=14.9 Hz)

EXAMPLE 12

N-(2,4,6-trimethoxyphenyl)-N'-(2-bromo-6,11-dihydrodibenz[b,e]oxepin-11-ylmethyl)urea (Compound 12)

1.0 g of Compound 12 was obtained in the same manner as in Example 1, except that 1.0 g of 2-bromo-6,11-dihydrodibenz[b,e]oxepin-11-acetic acid and 0.66 g of 2,4,6-trimethoxyaniline were used.

IR (KBr tablet; cm$^{-1}$): 3314, 1656, 1543, 1508, 1453, 1416, 1228

NMR (δ, ppm CDCl$_3$): 4.08 (t, 1H, J=7.4 Hz), 4.92 and 5.37 (q, 2H, AB type, J=14.8 Hz)

EXAMPLE 13

N-(2,6-diisopropylphenyl)-N'-(2-methoxy-6,11-dihydrodibenz[b,e]oxepin-11-ylmethyl)urea (Compound 13)

0.92 g of Compound 13 was obtained in the same manner as in Example 1, except that 1.0 g of 2-methoxy-6,11-dihydrodibenz[b,e]oxepin-11-acetic acid and 0.75 g of 2,6-diisopropylaniline were used.

IR (KBr tablet; cm$^{-1}$): 3360, 2964, 1728, 1524, 1494, 1442, 1260

NMR (δ, ppm CDCl$_3$): 4.06 (t, 1H, J=7.6 Hz), 4.99 and 5.40 (q, 2H, AB type, J=15.5 Hz)

EXAMPLE 14

N-(3,5-di-tert-butyl-4-hydroxyphenyl)-N'-(2-bromo-6,11-dihydrodibenz[b,e]oxepin-11-ylmethyl)urea (Compound 14)

1.09 g of Compound 14 was obtained in the same manner as in Example 1, except that 1.0 g of 2-bromo-6,11-dihydrodibenz[b,e]oxepin-11-acetic acid and 0.80 g of 3,5-di-tert-butyl-4-hydroxyaniline were used.

IR (KBr tablet; cm$^{-1}$): 3734, 3292, 2960, 1639, 1607, 1559, 1484, 1228

NMR (δ, ppm CDCl$_3$): 4.15 (t, 1H, J=7.6 HZ), 4.92 and 5.37 (q, 2H, AB type, J=14.8 Hz)

EXAMPLE 15

N-(2,6-diisopropylphenyl)-N'-(2-bromo-4-dimethylamino-6,11-dihydrodibenz[b,e]oxepin-11-ylmethyl)urea hydrochloride (Compound 15)

1.98 g of N-(2,6-diisopropylphenyl)-N'-(2-bromo-4-dimethylamino-6,11-dihydrodibenz[b,e]oxepin-11-ylmethyl)urea was obtained in the same manner as in Example 1, except that 2.26 g of 2-bromo-4-dimethylamino-6,11-dihydrodibenz[b,e]oxepin-11-acetic acid and 1.28 g of 2,6-diisopropylaniline were used.

IR (KBr tablet; cm$^{-1}$): 3408, 2962, 1652, 1590, 1529, 1252

NMR (δ, ppm CDCl$_3$): 2.81 (s, 6H), 4.01 (t, 1H, J=7.6 Hz), 4.87 and 5.28 (q, 2H, AB type, J=15.2 Hz), 1.78 g of the resulting compound was dissolved in 10 ml of ethanol and to the solution was added 0.7 ml of ethanol containing 7.34M hydrochloric acid. The mixture was recrystallized from isopropanol-isopropylether to obtain 1.33 g of Compound 15.

IR (KBr tablet; cm$^{-1}$): 3420, 2966, 1702, 1661, 1549, 1473, 1232

EXAMPLE 16

N-(2,4,6-trimethoxyphenyl)-N'-[1-methyl-1-(6,11-dihydrodibenz[b,e]oxepin-11-yl)ethyl]urea (Compound 16)

0.85 g of Compound 16 was obtained in the same manner as in Example 1, except that 2.0 g of 2-methyl-2-(6,11-dihydrodibenz[b,e]oxepin-11-yl)propionic acid and 1.56 g of 2,4,6-trimethoxyaniline were used.

IR (KBr tablet; cm$^{-1}$): 3320, 2936, 1634, 1594, 1541, 1509, 1229

NMR (δ, ppm CDCl$_3$): 1.29 (s, 3H), 1.44 (s, 3H), 3.66 (s, 6H), 3.84 (s, 3H), 4.80 and 4.91 (q, 2H, AB type, J=15.7 Hz)

EXAMPLE 17

N-(2,4,6-trimethoxyphenyl)-N'-[1-methyl-1-(2-bromo-6,11-dihydrodibenz[b,e]oxepin-11-yl)ethyl]urea (Compound 17)

1.63 g of Compound 17 was obtained in the same manner as in Example 1, except that 2.0 g of 2-methyl-2-(2-bromo-6,11-dihydrodibenz[b,e]oxepin-11-yl)propionic acid and 1.22 g of 2,4,6-trimethoxyaniline were used.

IR (KBr tablet; cm$^{-1}$): 3328, 2936, 1638, 1593, 1543, 1229

NMR (δ, ppm CDCl$_3$): 1.27 (2, 3H), 1.40 (s, 3H), 3.69 (s, 6H), 3.83 (s, 3H), 4.80 and 4.99 (q, 2H, AB type, J=15.5 Hz)

Formulation Example 1

Tablets

Tablets comprising the following composition were prepared by an ordinary method.

| | |
|---|---|
| Compound 2 | 100 mg |
| Lactose | 60 mg |
| Potato Starch | 30 mg |
| Polyvinyl Alcohol | 2 mg |
| Magnesium Stearate | 1 mg |
| Tar Dye | trace |

Formulation Example 2

Powder

A powder comprising the following composition was prepared by an ordinary method.

| | |
|---|---|
| Compound 3 | 150 mg |
| Lactose | 280 mg |

What is claimed is:

1. A tricyclic compound represented by formula (I):

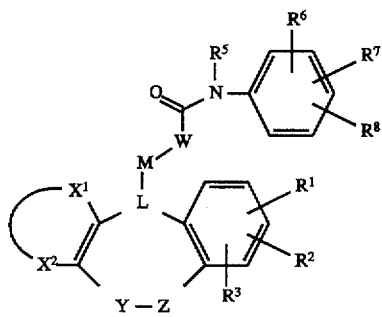

(I)

where $X^1$-$X^2$ represents CH=CH—CH=CH

Y—Z represents $CH_2$—O or $CH_2$—S;

L—M represents C=$CR^9$ (in which $R^9$ represents hydrogen or lower alkyl) or CH—$CR^{10}R^{11}$ (in which each of $R^{10}$ and $R^{11}$ independently represents hydrogen or lower alkyl);

W represents NR4 (in which R4 represents hydrogen or lower alkyl) or O, each of $R^1$, $R^2$ and $R^3$ independently represents hydrogen, lower alkyl, lower alkoxy, halogen, nitro, amino or mono- or di-lower alkyl-substituted amino;

$R^5$ represents hydrogen or lower alkyl;

each of $R^6$, $R^7$ and $R^8$ independently represents hydrogen, halogen, lower alkyl or lower alkoxy;

and a pharmaceutically acceptable salt thereto.

2. The compound according to claim 1, wherein Y—Z is $CH_2$—O, L—M is CH—$CH_2$ and W is NH.

3. The compound according to claim 2, wherein $R^5$ is hydrogen, one of $R^6$, $R^7$ and $R^8$ is 2-isopropyl, one of the remaining two is 6-isopropyl and the other is hydrogen.

4. N-(2,6-Diisopropylphenyl)-N'-(2-bromo-6,11-dihydrodibenz[b,e]oxepin-11-ylmethyl)urea or a pharmaceutically acceptable salt thereof.

5. N-(2,6-Diisopropylphenyl)-N'-(2-bromo-4-dimethylamino-6,11-dihydrodibenz[b,e]oxepin-11-ylmethyl)urea or a pharmaceutically acceptable salt thereof.

6. A pharmaceutical composition which comprises a pharmaceutically acceptable carrier and as the active ingredient, an effective amount of the compound as defined by claim 1.

7. The compound according to claim 3, wherein $R^1$, $R^2$ and $R^3$ are hydrogen.

\* \* \* \* \*